United States Patent
Xu et al.

(10) Patent No.: US 8,809,277 B2
(45) Date of Patent: Aug. 19, 2014

(54) DUAL SECURED THERAPEUTIC PEPTIDE DELIVERY SYSTEM

(75) Inventors: Peisheng Xu, Columbia, SC (US); Bindu Thapa, Columbia, SC (US); Bei Cheng, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 13/610,109

(22) Filed: Sep. 11, 2012

(65) Prior Publication Data
US 2013/0244953 A1   Sep. 19, 2013

Related U.S. Application Data

(60) Provisional application No. 61/626,019, filed on Sep. 19, 2011.

(51) Int. Cl.
*A61K 38/14* (2006.01)
*C07K 9/00* (2006.01)
*C12N 5/00* (2006.01)
*C12N 5/02* (2006.01)
*A61K 47/48* (2006.01)

(52) U.S. Cl.
CPC .................................. *A61K 47/4823* (2013.01)
USPC ........................... 514/20.9; 530/322; 435/375

(58) Field of Classification Search
CPC .............................. A61K 48/47; A61K 38/00
See application file for complete search history.

(56) References Cited

PUBLICATIONS

Wu et al "Disulfide-crosslinked chitosan hydrogel for cell viability and controlled protein release" Eur J Pharm Sci 37:198-206. Published online Feb. 10, 2009.*
Schmaljohann D "Thermo- and pH-responsive polymers in drug delivery" Advanced Drug Delivery Reviews 58:1655-1670. Published online Oct. 18, 2006.*
Kim et al "Self-assembed glycol chitosan nanoparticles for the sustained and prolonged delivery of antiangiogenic small peptide drugs in cancer therapy" Biomaterials 29:1920-1930. Published online Feb. 19, 2008.*
Ho et al "Self-organized nanoparticles prepared by guanidine- and disulfide-modified chitosan as a gene delivery carrier" J Materials Chem 21:16918-16927. Published Jul. 11, 2011.*
Xu et al "Zwitterionic chitosan derivatives for pH-sensitive stealth coating" Biomacromolecules 11:2352-2358. Published Sep. 13, 2010.*
Miles K and Matthew H "Improving a Biopolymer through Disulfide Cross-Linking of Chitosan Polymer Chains" 2010 Annual Meeting of the American Institute of Chemical Engineers. Presented Nov. 8, 2010.*
Khor E and Lim L "Implantable applications of chitin and chitosan" Biomaterials 24:2339-2349. Published Jun. 2003.*
Hoskin D.W.; Ramamoorthy, A. (2008) Studies on anticancer activities of antimicrobial peptides. *Biochemica Biophysica Acta*, 1778,357-375.
Papa, N.; Shai, Y. (2005) Host defense peptides as new weapons in cancer treatment. *Cellular and Molecular Life Sciences*, 62, 784-790.
Yang, L.; Harroun T.A.; Weiss, T.M.; Ding, L.; Huang, H.W. (2001) Barrel-Stave model or toroidal model? A case study on melittin pores. *Biophysical Journal*, 81, 1475-1485.
Pan, H.; Soman, N.R.; Schlesinger, P.H.; Lanza, G.M.; Wickline, S.A. (2011) Cytolytic peptide Nanoparticles ('NanoBees') for cancer therapy. *Nanomedicine and Nanobiotechnology*, 3, 318-327.
Soman, N. R.; Baldwin, S.L.; Hu, G., Marsh, J.N.; Lanza, G.M.; Heuser, J.E.; Arbeit, J.M.; Wickline, S.A.; Schlesinger, P.H. (2009) Molecularly targeted nanocarriers deliver the cytolytic peptide melittin specifically to tumor cells in mice, reducing tumor growth. *Journal of Clinical Investigation*, 119,2830-2842.
Tosteson T.M.; Tosteson, D.C. (1981) The sting melittin forms channels in lipid bilayers. *Biophysical Journal*, 36, 109-116.
Degrado, W.F.; Musso, G.F.; Lieber, M.; Kaiwer, E.T., Ktzey, F.J. ((1982) Kinetics and mechanism of hemolysis induced by melittin and by a synthetic melittin analogue. *Biophysical Journal*, 37, 329-338.
Bauhuber, S.; Rozsa, C.; Breunig, M.; Gopferich, A. (2009) Delivery of nucleic acids via disulfide-based carrier systems. *Advanced Materials*, 21, 3286-3306.
Lee, B.R.; Oh, K.T.; Oh, Y,T.; Baik, H.J.; Park, S.Y.; Youn, Y.S.; Lee, E.S. (2010) A novel pH-responsive polysaccharidic ionic complex for proapoptotic D-(KLAKLAK)2 peptide delivery. *Chemical communication*, 47,3852-3857.
Xu, P.; Bajaj, G.; Shugg, T.; Van, Alstine, W.O.; Yeo, Y. (2010) Zwittterionic chitosan derivatives for pH-sensitive stealth coating. *Biomacromolecules*, 11, 2352-2358.
Xu, P., Quick G. and Yeo, Y., (2009), Gene delivery through the use of a hyaluronateassociated intracellularlly degradable crosslinked polyethyleneimine. *Biomaterials*, 30, 5834-43.

* cited by examiner

*Primary Examiner* — Maury Audet
*Assistant Examiner* — Zachary J Miknis
(74) *Attorney, Agent, or Firm* — Dority & Manning, PA

(57) ABSTRACT

A delivery system is described that includes a polymer network that can incorporate a therapeutic peptide for targeted delivery to a cell, e.g., a cancer cell. The polymer network can secure the therapeutic peptide via two different mechanisms. First, a polymer of the network can interact with the therapeutic peptide via charge/charge interaction to form a complex with the peptide, thereby holding the peptide within the network. Second, the polymer network can be crosslinked, providing another level of securement for holding the therapeutic peptide within the network. The two levels of securement can be reversible, and following delivery of the network to the interior of a targeted cell reversal of the securement mechanisms can release the therapeutic peptide within the cell.

9 Claims, 3 Drawing Sheets

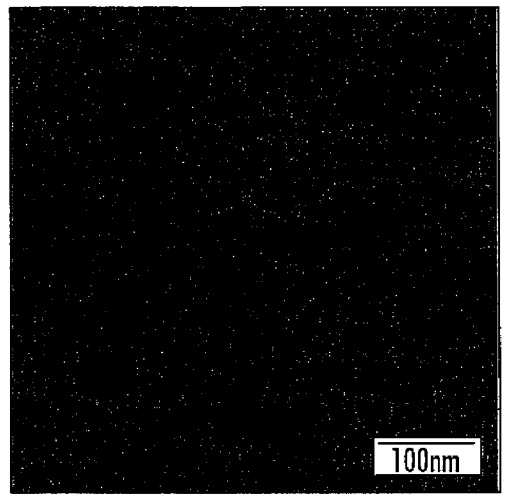
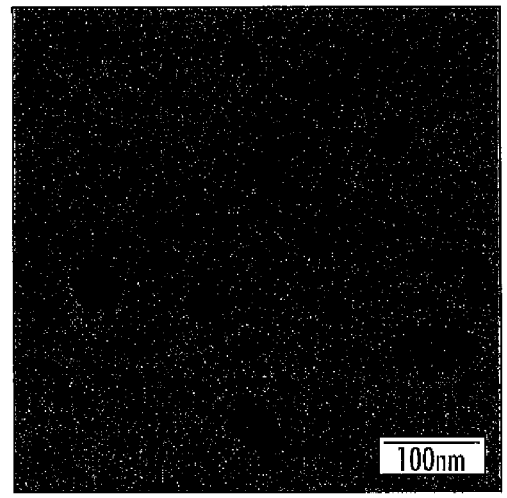
FIG. 4A      FIG. 4B
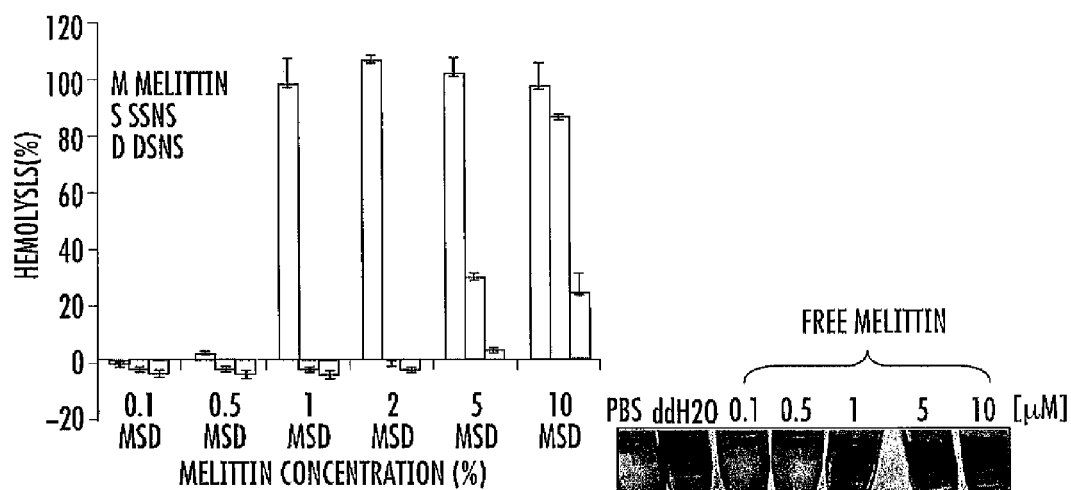
FIG. 5
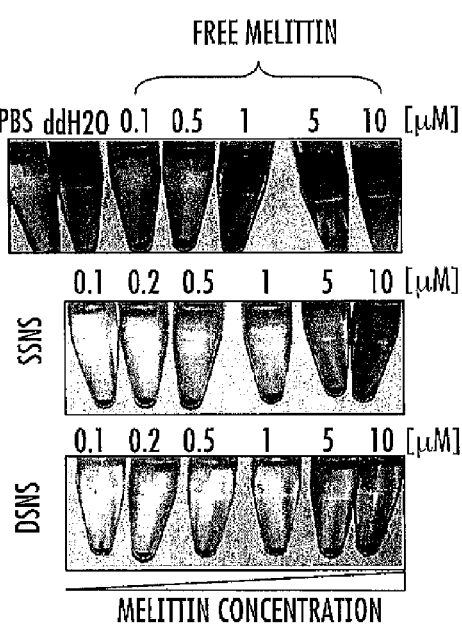
FIG. 6

DUAL SECURED THERAPEUTIC PEPTIDE DELIVERY SYSTEM

CROSS REFERENCE TO RELATED APPLICATION

The present application claims filing benefit of U.S. Provisional Patent Application Ser. No. 61/626,019 having a filing date of Sep. 19, 2011, which is incorporated herein by reference.

BACKGROUND

Host defense amphipathic peptides found in eukaryotic cells have diverse activity in humans and other species originating from their antibiotic, anticancer and anti-inflammatory activity. These peptides oligomerize with the phospholipid cell membrane and cell organelles that result in pore formation and subsequently cause cell death. Such peptides have been explored extensively for cancer therapy owing to their wide-spectrum lytic properties and because cancer cells are not likely to develop resistance to such materials. Unfortunately, in vivo application of these materials has been compromised by serious off-target toxicity.

Melittin, derived from the toxin of the honey bee, *Apis mellifera*, is one of the most promising amphipathic water-soluble α-helical cationic polypeptides. Melittin attacks the lipid membranes resulting in physical and chemical disruption of membrane structure leading to profound compromise of the cell permeability barrier by lysis. It is a very attractive cancer therapeutic agent because cancer cells are less likely to develop resistance to these peptides. Unfortunately, however, it is a nonspecific cytolytic peptide, and, as with other such peptides, this leads to off target-effects such as hemolysis when injected intravenously, thereby precluding any therapeutic benefits.

What is needed in the art is a drug-delivery system that can provide delivery of non-specific cytolytic peptides such as melittin to targeted tissues while preventing off-target effects. Such a system could be of great benefit in targeted drug-delivery, such as cancer therapy.

SUMMARY

According to one embodiment, disclosed is a drug delivery system that includes a crosslinked polymer network incorporating a therapeutic peptide. The network includes a stimuli responsive polymer complexed with the therapeutic peptide via charge/charge interaction. The stimuli responsive polymer is a zwitterionic polymer that exhibits a charge distribution that is dependent upon a characteristic of the local environment of the polymer. In addition, the crosslinked polymer network includes disulfide bonds.

Also disclosed is a method for forming the drug delivery vehicle. For example, a method can include grafting thiol groups on to a stimuli responsive polymer, forming a complex including the thiol-grafted stimuli responsive polymer and a therapeutic peptide, and crosslinking the thiol groups of the polymer to form a crosslinked network incorporating the therapeutic peptide.

Methods for delivering a therapeutic peptide to a cell are also disclosed. A method can include locating the crosslinked polymer network in an environment that contains the cell. The crosslinked polymer network can be taken up by the cell via endocytosis, and a characteristic of the environment within the cell can alter the charge distribution of the stimuli responsive polymer, leading to dissociation of the therapeutic peptide from the stimuli responsive protein. In addition, the disulfide bonds of the network can be cleaved within the cell, for instance via glutathione. The dissociation of the therapeutic peptide from the stimuli responsive polymer in conjunction with the cleavage of the disulfide bonds can release the therapeutic peptide from the network, allowing the therapeutic peptide to carry out the desired function within the cell, e.g., destruction of the cell.

BRIEF DESCRIPTION OF THE FIGURES

A full and enabling disclosure of the subject matter, including the best mode thereof, to one of ordinary skill in the art, is set forth more particularly in the remainder of the specification, including reference to the accompanying figures, in which:

FIG. 4A and FIG. 4B are transmission electron microscope (TEM) images of a polymer network prior to (FIG. 4A) and following (FIG. 4B) crosslinking of the network. Scale bars are 100 nm.

FIG. 5 graphically illustrates the hemolytic activity of free melittin, a polymer network that has not been crosslinked, and a crosslinked polymer network.

FIG. 6 presents images of materials included in the graph of FIG. 5.

DETAILED DESCRIPTION

Figure 1:
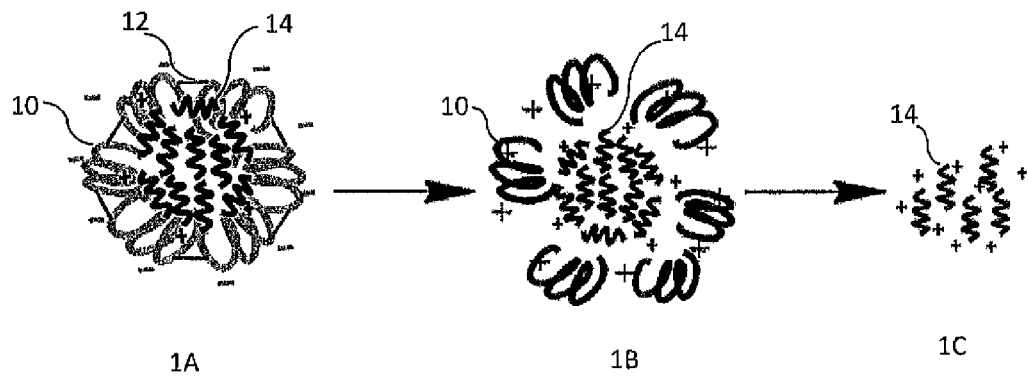
FIG. 1 is a schematic representation of a method of delivery of a therapeutic protein from a crosslinked polymer network as described herein.

The following description and other modifications and variations to the presently disclosed subject matter may be practiced by those of ordinary skill in the art, without departing from the spirit and scope of the present disclosure. In addition, it should be understood that aspects of the various embodiments may be interchanged in whole or in part. Furthermore, those of ordinary skill in the art will appreciate that the following description is by way of example only, and is not intended to limit the disclosure.

In general, disclosed herein is a delivery vehicle that includes a polymer network that can incorporate a therapeutic peptide for targeted delivery to a cell, e.g., a cancer cell. More specifically, the polymer network can secure the therapeutic peptide via two different mechanisms. First, a polymer of the network can interact with the therapeutic peptide via charge/charge interaction to form a complex with the peptide, thereby holding the peptide within the network. Second, the polymer network can be crosslinked, providing another level of securement for holding the therapeutic peptide within the network. The two levels of securement can be reversible, and following delivery of the network to the interior of a targeted cell reversal of the securement mechanisms can release the therapeutic peptide within the cell. Reversal of the securement mechanisms can be brought about due to the environment within the targeted cell and this reversal environment can be unique to the targeted cell. Thus, the peptide can be released within the targeted cell, but may not be released in a different cell that has a different inner environment. This specificity can prevent broad release of the therapeutic peptide and limit off-target effects of the peptide.

In one preferred embodiment, the delivery vehicle can be utilized to deliver a therapeutic peptide specifically to tumor tissue, and the therapeutic peptide can be an amphipathic peptide that can cause death of the cancer cells. The double securement of the crosslinked network can target deliver of the therapeutic peptide while sparing healthy cells, such as red blood cells as may be encountered during circulation. This embodiment can proved wide-spectrum anticancer effect on a variety of cancer cell types including, without limitation breast cancer cells, ovarian cancer cells, prostate cancer cells, lung cancer cells, liver cancer cells, brain cancer cells, skin cancer cells, or colon cancer cells.

Beneficially, due to the highly specific targeting capabilities of the system, the therapeutic peptide can be provided in relatively low concentrations. For example, more than about 90% of targeted cells, and 100% of the targeted cells in one embodiment, can be affected by use of a therapeutic peptide at a concentration of less than about 10 $\mu$M, for instance at a concentration of about 5 $\mu$M. Moreover, the same low concentration of therapeutic peptide can engender little or no effect on different cell types that are not targeted by the delivery system, i.e., those cell types in which the environment within the cell does not condone reversal of the securement mechanisms of the crosslinked polymer network.

The polymer network that incorporates and delivers the therapeutic peptide to a cell's interior can include a stimuli responsive polymer. These polymers reversibly alter their physico-chemical characteristics in response to the local environment. More specifically, the stimuli responsive polymer can be a zwitterionic polymer that exhibits a charge distribution. In addition, the charge distribution of the polymer can vary depending upon the local environment of the polymer. For instance depending upon the pH of the polymer environment, the polymer can exhibit a more or less negative surface charge distribution.

The stimuli responsive polymer can be a non-toxic, biocompatible polymer, and in one embodiment can be a biopolymer or can be derived from a biopolymer. As utilized herein, the term 'biopolymer' generally refers to a polymer that is produced by a living organism. In addition, the stimuli responsive polymer can be naturally zwitterionic or can be processed to develop the zwitterionic characteristic. By way of example, and without limitation, the stimuli response polymer can be a polymer derived from chitosan, or betaine polymers such as poly(carboxybetaine), poly(sulfobetaine), and so forth. Zwitterionic polymers derived from carboxybetaine and sulfobetaine have been described in U.S. Pat. No. 7,879,444 to Jiang, et al, which is incorporated herein by reference.

A biopolymer or biopolymer-based derivative such as glycol chitosan can be processed to form the stimuli responsive polymer through amidation of amine groups of the polymer with an anhydride, for instance through amidation of glycol chitosan with succinic anhydride. This process can introduce carboxyl groups to the polymer, and the resulting variation between amine protonation and carboxyl ionization with changes in pH can bring about a pH-dependent charge profile. The resulting pH responsive, zwitterionic glycol chitosan (SA-GCS) can exhibit a positive surface charge in environments having an acidic pH, for instance a pH of from about 6.8 to about 4.0, but will exhibit a negative surface charge in higher pH environments, for example in the environment of normal tissue and blood, which have pH values of about 7.4.

While pH can be a useful environmental characteristic for controlling the state of the zwitterionic polymer, particular in in vivo applications, pH need not necessarily be the environmental driving force that is used to alter the charge profile of the stimuli responsive polymer. For instance, temperature, electric field, magnetic field, etc. can be utilized to alter the charge profile of the stimuli responsive polymer and thereby control the complex formation and dissociation between the polymer and a therapeutic peptide.

In addition to the zwitterionic character of the stimuli responsive polymer, the polymer can include thiol groups that can be crosslinked following incorporation of the therapeutic protein into the network and thereby provide the second level of securement of the system. Addition of thiol functionality to the stimuli responsive polymer can be carried out according to any suitable process as is known in the art. For example, the stimuli responsive polymer can be reacted with N-Succinimidyl 3-[2-pyridyldithio]-propionate (SPDP) followed by cleavage of the 2-pyridyldithione, for instance by use of (tris (2-carboxyethyl)phosphine) (TCEP) to generate free thiol groups on the stimuli responsive polymer.

In another embodiment, carbodiiamide chemistry may be utilized. For instance reaction of the polymer with carbodiiamide in the presence of amidazole. The reaction product may then be reduced, such as by use of 2-mercaptoethanol to form the desired thiol functionality on the stimuli responsive polymer.

The stimuli responsive polymer including the thiol functionality can be utilized to form a crosslinked polymer network that incorporates any suitable therapeutic peptide for delivery to the targeted location. Therapeutic peptides encompassed herein can include amphipathic peptides as discussed above, but are in no way limited to such peptides. In general, any peptide that can form a complex with the stimuli responsive polymer under a first set of environmental conditions and that can dissociate from the polymer under a second set of environmental conditions due to the altered charge profile of the polymer at those conditions can be incorporated within and delivered by the crosslinked polymer network. By way of example, a variety of insect venoms and snake venoms have been hypothesized to contain amphipathic peptides that may be incorporated in the system. Synthetic peptides formed to include a charge distribution can also be utilized.

As utilized herein, the terms "peptide" and "polypeptide" are interchangeable and indicate a molecular chain of amino acids without reference to a specific length of the product. Thus, di-peptides, oligopeptides and proteins are included within the definition of peptide. This term is also intended to include peptides that have been subjected to post-expression modifications such as, for example, glycosylations, acetylations, phosphorylations and the like.

The therapeutic peptide can be modified so as to better form a complex with the stimuli responsive polymer or can be unmodified. In either case, the formation of a complex between the therapeutic peptide and the stimuli responsive polymer can serve to protect the therapeutic peptide from possible side reactions prior to delivery. Formation of the complex and crosslinking of the network can prevent undesired off target effects of the therapeutic peptide, as discussed above, but can also protect the therapeutic peptide from interaction with other materials prior to the targeted delivery of the peptide. For example, the protective association can be established so as to hold the therapeutic peptide in an unreactive state and protect the peptide from reaction with and possible destruction by materials that may be encountered during circulation of the network and prior to delivery of the therapeutic peptide from the crosslinked network, e.g., immune system agents that could otherwise destroy the peptide prior to delivery.

Complexation of the therapeutic peptide with the stimuli responsive polymer can generally be carried out simply via incubation of the two under suitable conditions (e.g., pH, temperature, etc.). Following formation of the complex, the polymer can be crosslinked through oxidation of the thiol groups to form the crosslinked polymer network incorporating the therapeutic peptide.

The crosslinked polymer network can be delivered to a site that includes the targeted cell types according to any suitable delivery mechanism. For example, when considering an in vivo delivery, the crosslinked polymer network can be injected and delivered via the circulatory system, can be inhaled for delivery via the respiratory system, can be implanted as a component of an implantable device or delivery vehicle, or can be ingested for delivery via the digestive system. Other modes of in vivo delivery are likewise encompassed herein such as, without limitation, topical delivery, transdermal delivery, intramuscular delivery, and so forth.

The crosslinked network can be administered in combination with a pharmaceutically acceptable vehicle such as an inert diluent or an assimilable edible carrier. For example, when considering oral delivery, it may be enclosed in hard or soft shell gelatin capsules, may be compressed into tablets, or may be incorporated directly with food. For oral therapeutic administration, the crosslinked network may be combined with one or more excipients and used in the form of ingestible tablets, buccal tablets, troches, capsules, elixirs, suspensions, syrups, wafers, and so forth.

An oral delivery vehicle may additionally include one or more of the following, without limitation: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and so forth. The crosslinked network may be suspended in a syrup or elixir that can contain sucrose or fructose as a sweetening agent, methyl and propylparabens as preservatives, a dye and flavoring. Of course, any material used in preparing any unit dosage form should be pharmaceutically acceptable and substantially non-toxic in the amounts employed.

When considering delivery according to a method such as intravenously or intraperitoneally by infusion or injection, suspensions of the crosslinked network can be prepared in water or saline and optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

A delivery form suitable for injection or infusion can include sterile aqueous solutions or dispersions or sterile powders comprising the crosslinked network and adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the maintenance of the particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

For topical administration, the crosslinked network may be applied directly to the skin or a wound or suspended in liquid and then applied. The crosslinked network can also be administered to the skin as compositions or formulations, in combination with a dermatologically acceptable carrier, which may be a solid or a liquid.

Useful solid delivery vehicles include wound dressings, bandages, and the like that can have an absorbent material into which the crosslinked network can be impregnated. Useful liquid carriers include water, alcohols or glycols or water-alcohol/glycol blends, in which the crosslinked network can be dispersed at effective levels, optionally with the aid of non-toxic surfactants. Adjuvants such as antimicrobial agents can be added to optimize the properties for a given use. The resultant liquid compositions can be applied from absorbent pads, used to impregnate bandages and other dressings, or sprayed onto the affected area using pump-type or aerosol sprayers.

Upon delivery of the crosslinked network to an environment in which the targeted cell is located, the crosslinked network can be taken up by the cell according to typical endocytosis pathways including clathrin-mediated endocytosis, caveolae, macropinocytosis, and phagocytosis.

FIG. 1 is a schematic illustration of delivery of a therapeutic peptide from the crosslinked polymer network. FIG. 1A presents the formed crosslinked network including the therapeutic peptide 14, which in this particular embodiment displays a net positive charge, encapsulated within the network that includes the stimuli responsive polymer 10 displaying a net negative charge and crosslinked via disulfide bonds 12. The charge/charge interaction and the disulfide bond crosslinks together preventing premature release of the therapeutic peptide during circulation. At FIG. 1B, following endocytosis of the crosslinked polymer network, intracellular glutathione (GSH) cleaves disulfide bond and the lysosomal pH transforms the surface charge of the stimuli responsive polymer 10 to a net positive charge. Upon alteration of the surface charge, the complex formed between the therapeutic peptide 14 and the stimuli responsive polymer 10 dissociates and the therapeutic peptide 14 is released into the cell interior as shown at FIG. 1C.

The delivery system can be suitable for both in vivo and in vitro applications. For instance, in one embodiment, the systems can be utilized in treatment or prevention of disease in an individual, providing targeted delivery of a therapeutic peptide to particular cell types. In another embodiment, the disclosed system can be utilized in vitro, for instance in tissue engineering applications. For example, the delivery system can be utilized to provide for the targeted delivery of therapeutic peptides to a developing cellular system. The delivery system can be utilized to deliver pharmaceutically useful therapeutic peptides including destructive agents such as amphipathic peptides as well as growth and nutrient agents that can encourage the healthy development of a biological system, including the development of individual cells in tissue engineering applications.

The disclosure may be further understood with reference to the Example, set forth below.

EXAMPLE

Preparation of Polymer

Figure 2:
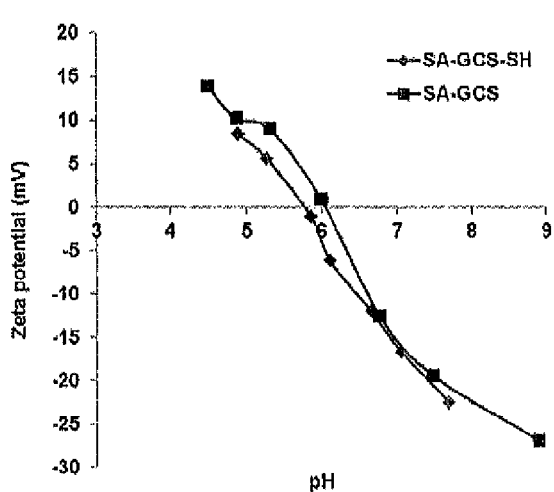
FIG. 2 presents the pH-dependent zeta potential of amidized glycol chitosan (SA-GCS) and thiolated glycol chitosan (SA-GCS-SH). The isoelectric points (IEP) were 6.05 and 5.80, respectively.

Glycol chitosan (MW: 200 KDa) was depolymerized to Mw 28 kDa using potassium persulfate and employed to prepared thiol grafted zwitterionic polymer using N-Succinimidyl 3-[2-pyridyldithio]-propionate (SPDP) and succinic anhydride, respectively. Succinic anhydride was grafted onto the glycol chitosan (28 kDa) by amidation. Briefly; glycol chitosan (30 mg) was reacted with succinic anhydride (4.17 mg) at room temperature. After 2 hours of stirring, the pH of the reaction was adjusted to 8 and stirred for another 2 hours. The final product was purified by dialysis (Spectra 7 MWCO: 3500 Da) against distilled water at pH 9 and collected by lyophilization for 48 hours. Isoelectric point (IEP) of the polymer was calculated using $\zeta$-potential measured at different pH levels (FIG. 2).

To graft thiol groups, amidized glycol chitosan was reacted with SPDP and then cleaved by tris(2-carboxyethyl)phosphine (TCEP). Amidized glycol chitosan (60 mg) was reacted with 21.63 mg of SPDP N-hydroxysuccinimide ester in dimethyl sulfoxide (10 ml) at room temperature in the presence of triethylamine (300 µl). After overnight reaction, TCEP (39.58 mg) was added and stirred for 3 h at room temperature to cleave disulfide bonds of the grafted SPDP, which removes 2-pyridinethione, generating free thiol group in polymer. Following, the material was purified by dialysis (Spectra 7 MWCO: 3,500 Da) against 10 mM Ethylenediaminetetraacetic acid (EDTA) followed by DI water. The content of thiol group was quantified by DTNB (5,5'-Dithio-bis(2-nitrobenzoic acid)) assay. Isoelectric point (IEP) of the thiolated polymer was calculated using $\zeta$-potential measured at different pH levels (FIG. 2).

Formation of Complexes:

The thiol grafted zwitterionic glycol chitosan was employed for the preparation of complexes with melittin. Briefly, 1 ml of melittin (0.1 mg/ml) was incubated with different amounts (0.1 to 4 ml) of polymer (5 mg/ml) in TRIS buffer (pH 7.4) at room temperature for 1 hour to form the single secured complexes (single secured nano-stings—SSNS) of different ratios. To develop crosslinked double secured complexes (double secured nano-stings—DSNS), SSNS was aerially oxidized for 2 hours at room temperature. The binding efficiency was measured by measuring the fluorescence of free melittin (EX: 280 nm, EM: 350 nm) in complexes prepared in TBS at pH 7.4 and room temperature. To evaluate the biological activity, SSNS and DSNS were prepared at a polymer:melittin weight ratio of 200:1.

Figure 3:
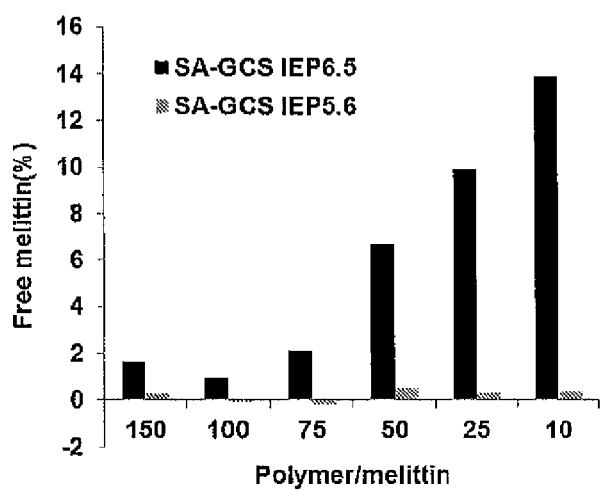
FIG. 3 presents the binding efficiency of two SA-GCS polymers with melittin.

FIG. 3 graphically presents the binding efficiency results of two SA-GCS polymers formed with different amounts of succinic anhydride. As expected, the polymer modified with a lower amount of succinic anhydride demonstrated a higher IEP and a lower binding efficiency. (Data on the graph represent mean±SD, n=3.)

Hydrodynamic size, surface charge and morphology were measured through DLS and TEM, respectively. FIG. 4A presents a TEM image of the single secured complexes (SSNS) and FIG. 4B presents a TEM image of the double secured complexes (DSNS).

Hemolytic Assay:

Rat blood was used to compare hemolytic effects of free melittin, SSNS, and DSNS using DI water as positive control and PBS as negative control. Briefly, rat red blood cells were washed using 210 mM sodium chloride and dispersed in phosphate buffer saline (pH 7.4). To the SSNS, DSNS and free melittin corresponding to melittin concentration of 0.1 to 10 µM, the same amount of red blood cells was added and incubated at 37° C. for 1 hour. Following, each sample was centrifuged at 300 rcf for 2 min. and the optical density of supernatant was measured ($\lambda$=405 nm.) for the quantification of lysed cell amount. The results are shown graphically in FIG. 5 and in the corresponding photographs of FIG. 6. As can be seen, the free melittin is highly lytic and completely lysed the cells at 1 µM concentrations (FIG. 6, top). The DSNS displayed significantly less red blood cell lysys, having negligible hemolysis (<5%) at 5 µM, which also provides anticancer activity.

MTT Assay:

The anticancer activity of SSNS and DSNS in MCF-7, HCT-116, SKOV and NCI/ADR-res cancer cell lines were evaluated by 3-(4,5-dimethylthiazol-2-yl)-2,5-diphenyltetrazolium bromide (MTT) assay using melittin as a positive control and non-treated cell as a negative control. The cells were seeded in 96-well plates at an initial density of 12,000 cells/well in 150 µl of DMEM medium supplemented with 100 U penicillin/streptomycin and 10% FBS. After 24-hour of incubation, the medium was replaced with 150 µl of fresh medium containing SSNS, DSNS and melittin (corresponding to 0.1 to 10 µM melittin). After 24 hour incubation, the MTT reagent and stop solution were added and the optical density was measured using a microplate reader (ELX808, Bio-Tech instrument, Inc) at $\lambda$=595 nm. Data represent mean±SD, n=3. Cell viability was expressed as relative to the reference standard.

Figure 7A:
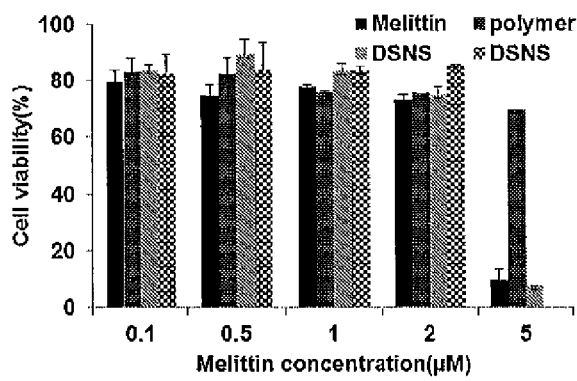
FIGS. 7A-7D graphically present the anti-cancer activity of free melittin, a polymer network that has not been crosslinked, and a crosslinked polymer network in different cell lines including MCF-7 breast cancer cell line (FIG. 7A), HCT-116 colon cancer cell line (FIG. 7B), SCOV-3 ovarian cancer cell line (FIG. 7C), and NCI/ADR-res ovarian cancer cell line (FIG. 7D).
Figure 7B:
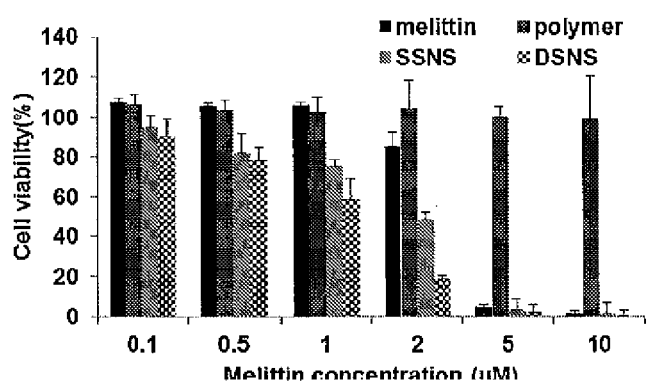
Figure 7C:
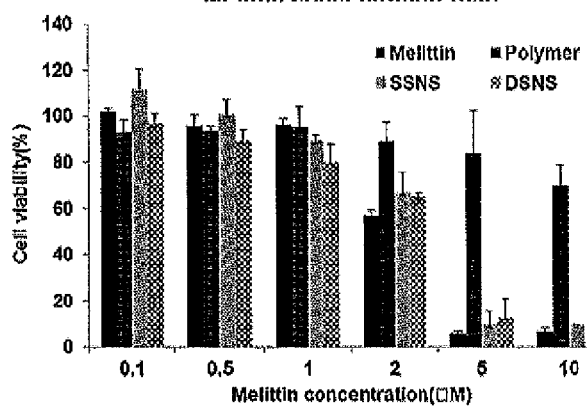
Figure 7D:
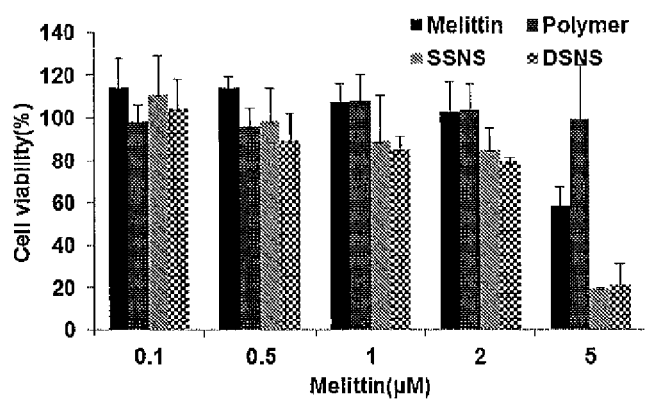

Results are shown in FIGS. 7A-7B. As can be seen, the DSNS killed 100% MCF7 and HCT-116 cells and about 80% SKOV-3 and NCI/ADR-Res cells at the melittin concentration of 5 µM, which is equivalent to that needed for free melittin. Significantly, DSNS didn't show significant hemolytic activity at this concentration.

Those skilled in the art will readily appreciate that many modifications are possible in the exemplary embodiments that have been described in detail above without materially departing from the novel teachings and advantages of this disclosure. Accordingly, all such modifications are intended to be included within the scope of this invention which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A drug delivery system comprising a crosslinked polymer network that incorporates an amphipathic water-soluble α-helical cationic peptide, the crosslinked polymer network comprising a stimuli responsive polymer complexed with the amphipathic water-soluble α-helical cationic peptide via charge/charge interaction, the stimuli responsive polymer being a zwitterionic amidized glycol chitosan polymer having a charge distribution that varies depending upon a characteristic of the local environment of the stimuli responsive polymer, the crosslinked polymer network further including disulfide bonds that crosslink the polymer network via thiol groups of the zwitterionic amidized glycol chitosan polymer wherein the amphipathic water-soluble α-helical cationic peptide is melittin.

2. The drug delivery system of claim 1, wherein the characteristic of the local environment is pH.

3. A method for delivering the amphipathic water-soluble α-helical cationic peptide to the interior of a cell comprising locating the crosslinked polymer network of claim 1 in an environment containing the cell, endocytosis of the crosslinked polymer network by the cell moving the crosslinked polymer network into the interior of the cell, wherein a pH level within the cell alters the charge distribution of the stimuli responsive polymer such that the amphipathic water-soluble α-helical cationic peptide dissociates from the stimuli responsive protein within the cell, the environment within the cell comprising glutathione that cleaves the disulfide bonds that crosslink the polymer network.

4. The method according to claim 3, wherein the cell is a cancer cell.

5. The method according to claim 4, wherein the cancer cell is a breast cancer cell, an ovarian cancer cell, a prostate cancer cell, a lung cancer cell, a liver cancer cell, a brain cancer cell, a skin cancer cell, or a colon cancer cell.

6. The method according to claim 3, wherein the step of locating the crosslinked polymer network in the environment containing the cell comprises delivering the crosslinked polymer network to the environment according to an infusion process or by an injection.

7. The method according to claim 3, wherein the step of locating the crosslinked polymer network in the environment containing the cell comprises implanting the crosslinked polymer network.

8. A method for forming a drug delivery vehicle comprising:
grafting thiol groups on to a stimuli responsive polymer, the stimuli responsive polymer being a zwitterionic amidized glycol chitosan polymer;
forming a complex including the thiol-grafted stimuli responsive polymer and an amphipathic water-soluble α-helical cationic peptide, the thiol-grafted stimuli responsive polymer and the amphipathic water-soluble α-helical cationic peptide being complexed to one another via charge/charge interactions wherein the amphipathic water-soluble α-helical cationic peptide is melittin; and
crosslinking the thiol groups of the polymer to form a crosslinked network incorporating the amphipathic water-soluble α-helical cationic peptide.

9. The method of claim 8, further comprising combining the crosslinked network with a pharmaceutically acceptable vehicle.

* * * * *